US006749875B2

(12) United States Patent
Selleck

(10) Patent No.: US 6,749,875 B2
(45) Date of Patent: Jun. 15, 2004

(54) FRUIT AND VEGETABLE PRESERVATIVE

(75) Inventor: Rhonda Selleck, Barham (AU)

(73) Assignee: Citrus Sensation, Pty. Ltd., New South Wales (AU)

( * ) Notice: Subject to any disclaimer, the term of this patent is extended or adjusted under 35 U.S.C. 154(b) by 168 days.

(21) Appl. No.: 09/944,198

(22) Filed: Sep. 4, 2001

(65) Prior Publication Data

US 2002/0054950 A1 May 9, 2002

Related U.S. Application Data

(63) Continuation-in-part of application No. PCT/AU00/01041, filed on Sep. 4, 2000.

(51) Int. Cl.⁷ .............................. A23C 7/154; A23L 2/44
(52) U.S. Cl. ...................... 426/270; 426/310; 426/324; 426/330.5; 426/599
(58) Field of Search ................................. 426/270, 310, 426/324, 330.5, 599

(56) References Cited

U.S. PATENT DOCUMENTS

| 6,403,139 B1 | * | 6/2002 | Sardo et al. | 426/541 |
| 2002/0127312 A1 | * | 9/2002 | McArdle et al. | 426/262 |

FOREIGN PATENT DOCUMENTS

| EP | 0 402 049 | | 12/1990 |
| EP | 0 420 376 | | 4/1991 |
| FR | 2745977 | * | 12/1996 |
| JP | 362126931 A | * | 6/1987 |
| JP | 402100660 A | * | 4/1990 |
| JP | 3200781 | | 9/1991 |
| JP | 08228685 | | 9/1996 |
| JP | 408332024 A | * | 12/1996 |
| JP | 408332024 | * | 12/1996 |
| JP | 11117193 | | 4/1999 |
| JP | 2938009 | | 8/1999 |
| JP | 11299452 | | 11/1999 |

OTHER PUBLICATIONS

Hawley, G. The Condensed chemical Dictionary, 10$^{th}$ Ed. 1981, Van Nostrand Reinhold Co., pp. 466, 796.*

* cited by examiner

Primary Examiner—Helen Pratt
(74) Attorney, Agent, or Firm—Connolly, Boye, Lodge & Hutz LLP

(57) ABSTRACT

Minimally processed fruits and vegetables are preserved by use of a flavonoid. Cut and peeled fruits or vegetables are sprayed or dipped in a solution containing a flavonoid and an anti-oxidant such as ascorbic acid, erythorbic acid or alpha lipoic acid. Juices are also preserved by the addition of a flavonoid and ascorbic acid if it is not already present.

10 Claims, No Drawings

FRUIT AND VEGETABLE PRESERVATIVE

CROSS REFERENCE TO RELATED APPLICATION

The present application is a continuation-in-part of International Application No. PCT/AU00/01041, filed Sep. 4, 2000.

This invention relates to the preservation of minimally processed fruits and vegetables and flowers, particularly cut and peeled or juiced fruits and vegetables.

BACKGROUND OF THE INVENTION

Most fruits and vegetables are subject to discolouration and spoilage once they are cut and peeled. This is usually due to enzymatic and bacterial action.

Patent application WO 97/16976 discloses a method of storing cut apple pieces in which whole apples are washed in chlorinated water to inactivate microorganisms, the apples are then cored, peeled and sliced and immersed in an ascorbic acid solution having a pH of 2.2 to 2.7 and are then drained and stored in modified atmosphere containers.

Patent application WO 99/34683 discloses a method of treating cut fresh vegetables by dipping in a solution containing calcium ions and ascorbate or erythorbate ions.

U.S. Pat. No. 6,054,160 treats cut apples with a solution containing L-cysteine, sorbitol, and calcium chloride and then stores them in a modified atmosphere pack.

These treatments provide a shelf life of up to 2 weeks but in practice this is not long enough.

It is an object of this invention to provide an improvement in shelf life for minimally processed fruit and vegetables.

BRIEF DESCRIPTION OF THE INVENTION

To this end the present invention provides a process of extending the useful shelf life of minimally processed fruits and vegetables which includes the step of treating the fruits and vegetables with a flavonoid compound.

This invention is partly predicated on the discovery that the presence of flavonoids inhibits the enzymatic and bacterial action that leads to discolouration and spoilage. The flavonoid may be added to a solution sprayed or dipped on to the processed fruits or vegetables or added to the fruit or vegetable juice.

Flavonoids such as proanthocyanidin have been identified as antioxidants and recommended as food additives for nutriceutical use but not to prevent deterioration in minimally processed fruits and vegetables.

It is preferred that an anti oxidant such as ascorbic acid, erythorbic acid, lipoic acid including alpha lipoic acid, be present with the flavonoid compound. It is believed that these compounds act synergistically with the flavonoid compounds to inhibit oxidation of the minimally processed fruits and vegetables. Some fruits and vegetables have an adequate content of ascorbic acid and for these addition of a flavonoid is sufficient.

Throughout this specification minimally processed means the steps of processing raw, uncooked fruits, nuts and vegetables for storage and/or transport prior to eating or further processing. This includes peeling, coring, slicing and juicing.

Throughout this specification flavonoid means a polyphenol compound of the type having at least two aromatic rings which occur widely in the plant kingdom and inhibits oxidation. These compounds may also form polymeric compounds with the flavonoid repeating unit. The term flavonoid as used throughout this specification includes individual flavonoids, mixtures and plant extracts having a high flavonoid content.

The fruits to which this invention is applicable include oranges, mandarins, grapefruit, tangerines, tangellos, pomellos, kiwi fruit, mango, pineapple, apricots, strawberries, blackberries, raspberries, mulberries, cherries, blueberries, grapes, figs, peaches, nectarines, apples, pears, nashi, plums, tamarillo, cantaloupe, guavas, lychees, rumbutans, melon, passionfruit, avocado and mangosteen. Nuts such as chestnuts may also be treated.

The vegetables which can be treated according to this invention include broccoli, brussel sprouts, carrot, cabbage, capsicum, chili, chocos, cauliflower, celery, lettuce, garlic, ginger, green beans, shelled peas, asparagus, corn, pumpkin, mushrooms, snow peas, zucchini.

The fruit or vegetables are sprayed or immersed in the solution containing the flavonoid and excess solution is removed from the surfaces and the products are packaged in the usal way for minimally processed fruits and vegetables.

Fruit juice can be preserved by the addition of flavonoids to the juice. Navel oranges are usually not preferred for juicing because the juice acquires a bitter taste. The addition of a flavonoid to navel orange juice inhibits the development of this bitter taste. In preparing the fruit juice the pulp is usually separated from the serum and then recombined to form the juice. The flavonoid may be added to either the pulp or the serum or both but preferably to the pulp.

In another aspect of this invention the present invention provides a preservative composition for use in preserving minimally processed fruits and vegetables which composition includes a flavonoid mixed with a food grade anti oxidant, preferably selected from one or more of ascorbic acid, erythorbic acid, lipoic acid including alpha lipoic acid and salts thereof such as sodium, potassium and calcium ascorbate. This is preferably a powder but may be a liquid concentrate that can be diluted in water, tea infusion or a fruit juice to form the dipping solution. The ratio of flavonoid to antioxidant is usually from 1:50 to 1:150 by weight. This mixture is then diluted in 30 to 50 times its weight in water or fruit juice. The flavonoid content in the dipping solution or in juiced fruit or vegetable is preferably from 0.01 wt % to 0.1 wt %. In addition to the flavonoid, alpha lipoic acid may also be added to the dipping solution or fruit or vegetable juice as an additional antioxidant in amounts from 0.0005 wt % to 0.005 wt %.

The flavonoid may be any available compound or extract. The group takes its name from the compounds flavone, flavonol, flavanone but also includes chalcones, anthocyanidins, proanthocyanidins, isoflavonoidsand polymeric forms of these compounds. Flavonoids are available as plant extracts and are an effective source for use in this invention. A preferred flavonoid source is an extract from pinus radiata or pinus pinasta [maritime pine] marketed as Enzogenol™ and Pyncogenol™ respectively. Enzogenol contains about 38% polymeric proanthocyanidins, 25% oligomeric proanthocyanidins and 22% monomer, dimer and trimer proanthocyanidins. Grape seed extract and grape seed oils are another favoured source. Also may be mentioned Quercitin, a flavonoid present in grapes, apples, broccoli and onions, acerola from cherries, hesperidin, rutin and any plant extracts rich in flavonoids such as citrus seed extract, cranberry extract, juniper berry extract, rose hip extract.

The dipping or spraying solutions may contain other ingredients for flavour and to assist the action of the flavonoids. Acid to maintain a low pH for antibacterial effectiveness is a useful ingredient and any food grade acid such as citric acid may be used. Alternatively acidic fruit juices, such as pineapple juice, may be used. Other ingredients may include sugar, water sanitisers such as colloidal silver, or microhydrin.

DETAILED DESCRIPTION OF THE INVENTION

Preferred formulations and treatments for particular products will be described with reference to particular fruits and vegetables Oranges The orange is peeled, cored and the outer membrane is removed.

The dipping solution is made proportionately to the formula:

| | |
|---|---|
| Unsweetened pineapple juice | 400 ml |
| Sugar | 400 g |
| Grape seed oil | 20 ml |

The sugar and pineapple juice are boiled together for 3 minutes cooled and the grape seed oil is added.

The peeled and cored orange is immersed for about 3 minutes and then the excess solution is allowed to drain and the orange can be packed into a suitable display container.

An alternative formula may replace the grapeseed oil with about 60 mg of pyncogen or enzogen which are pine bark extracts containing a high is concentration of flavonoid compounds including polymeric proanthocyanidins.

A preferred formula is
Unsweetened pineapple juice 400 ml boiled for 3 minutes with 400 g sugar then cooled. To which is added 20 ml grapeseed oil and 60 mg enzogenol.

Shelf life trials of the oranges so treated indicated that even after eight weeks the taste and flavour remained fresh.

Orange Juice

Navel oranges were juiced and three samples were produced as shown in table 1

| Sample | Navel juice | pyncogenol ™ | enzogenol ™ |
|---|---|---|---|
| 1 | 200 ml | | |
| 2 | 200 ml | 20 mg | |
| 3 | 200 ml | | 40 mg |

The control sample 1 showed distinct bitterness after two weeks storage but the samples 2 and 3 were still tasting fresh and sweet after three weeks.

A preferred flavonoid for orange juice may be selected from citrus bioflavonoids, tangeretin, hesperidin, rutin or mixtures thereof.

In addition to the flavonoid alpha lipoic acid may also be added to the orange juice as an additional antioxidant in amounts from 0.0005 wt % to 0.005 wt % of the orange juice.

A preferred additive for orange juice is:

30 mg alpha lipoic acid
5 mg Folic acid
30 mg pyonogenol or grape seed extract or a mixture.
100 mg of citrus bioflavonoids
25 mg hesperidin
50 mg Rutin
and 200–250 mg zinc-gluconate.

This formula is particularly effective with navel oranges. Navel orange juice after eight weeks storage had a fresh citrus smell and bright orange colour and was still pleasant tasting with no aftertaste.

Apples

A dipping solution for apples is prepared by boiling 400 ml of water with 20 g of sugar for three minutes and allowing to cool. To the sugar solution is added 20 mg of Enzogenol™ and 60 ml of lemon juice or 20 mg ascorbic acid.

Granny smith apples which had been peeled and sliced are immersed in this solution for about 10 minutes while softer apples are immersed for 8 minutes. The apples are removed drained and packed for cold storage. After 3 weeks the pieces are still white and crisp.

A more complete formula for apples is prepared by using a dry mix of ascorbates and flavonoids containing

| | |
|---|---|
| 600 mg magnesium ascorbate | 25 mgs of acerola |
| 750 mg calcium ascorbate | 12 mgs of rose hip powder [rosa canina] |
| 600 mg potassium ascorbate | 25 mgs bioflavonoids |
| | 37 mgs hesperidin |
| | 50 mg rutin |
| | 6 mg maritime pine bark extract. |

This powder is added to a solution of 600 ml water which has been boiled for 3 minutes with 200 g of sugar, allowed to cool and mixed with 50 mls of unsweetened pineapple juice.

By immersing the peeled and quartered apples in this solution for 12 minutes followed by draining and packing a shelf life of 3 weeks was achieved.

Using this formula it is possible to prolong storage of the apples by allowing the peeled and quartered apples to remain in solution or to be immersed and drained alternately for an hour repeatedly for as long as needed until the pieces are to be packed for transport.

A comparative test was carried out with apples in which group 1 were treated with a solution from which the pineapple juice and ascorbates had been omitted while group 2 were treated with the complete solution but without the addition of flavonoids.

After 17 days storage the group 1 apple slices were still normal in colour and crisp while the group 2 apple slices were rated as fairly crisp and brown in appearance.

Apple Juice

Apples were juiced and three samples were produced as in table 2

| Sample | Apple Juice | Ascorbic acid | pyncogenol ™ | enzogenol ™ |
|---|---|---|---|---|
| 1 | 200 ml | | | |
| 2 | 200 ml | 5 g | 20 mg | |
| 3 | 200 ml | 5 g | | 40 mg |

The juice of sample 1 oxidised and became brown. After 4 weeks the condition of samples 2 and 3 were still fresh.

A preferred apple juice formula used per lire of fresh apple juice consists of 200 ml of pure water
5 g calcium ascorbate,
1 mg Quercitin
20 mg enzogenol or 50 mg grapeseed extract.

Other Fruits

Formulae for some other fruits are set out in table 3

The water and sugar are boiled for 3 minutes then cooled and the remaining ingredients are added.

The fruits are peeled if needed and cut to remove seeds if necessary and the prepared fruits are immersed for 3 to 8 minutes on average. Strawberries are preferably dipped quickly and packed.

Modified atmosphere packaging was used for all the packed fruit.

TABLE 3

| FRUIT | Solution | Ascorbic acid source | Flavonoid | other |
|---|---|---|---|---|
| Nashi | 400 ml water + 100 g sugar | 15 ml lemon juice | 20 mg enzogenol | |
| Honey dew melon | 400 ml water + 100 g sugar | 10 ml lemon juice | 10 mg enzogenol | |
| Pineapple | 300 ml water + 200 g sugar | 7.5 g calcium ascorbate + 30 ml lemon juice | 60 mg enzogenol | 10 ml sanitizer |
| Canteloupe | 500 ml water | 250 mg calcium ascorbate | 6 gms maritime pine extract | 5 ml sanitizer |
| Strawberries | 500 ml water + 5 ml fruit sugar | | 5 mg rosehip powder | 5 ml sanitizer + 125 mg silica hydride |
| Nectarines or Apricots | 400 ml water + 200 g sugar | 5 g calcium ascorbate + 45 ml lemon juice | 12 mg maritime pine extract or 60 mg enzogenol | 5 ml sanitizer + 125 mg silica hydride |
| mangosteens | 200 ml water + 10 g sugar + 125 ml unsweetened pineapple juice | 125 ml grapefruit juice | 60 mg enzogenol + 25 ml grapeseed oil | 5 ml sanitizer + 125 mg silica hydride |
| Durian | 50 ml unsweetened pineapple juice + 50 g sugar | 5 g calcium ascorbate | 50 mg bioflavonoids + 25 mg hesperidin + 25 mg rutin + 60 mg enzogenol | 10 ml grapeseed oil or glycerin |
| Chestnuts | 200 ml water + 5 mg green tea | 5 g calcium ascorbate | 90 mg enzogenol | |
| Chestnuts | 400 ml water | 60 ml lemon juice | 60 mg enzogenol | |
| peaches | 350 ml water + 150 g sugar | 5 g calcium ascorbate + 40 ml lemon juice | 12 mg maritime pine extract or 60 mg enzogenol | 5 ml sanitizer + 125 mg silica hydride |

Using these formulas in the process of this invention extended the usual shelf life of all these fruits to beyond 3 weeks.

The fruits treated with these formulae can also be used in fruit salads. The apple formula can be used with salads containing two or more of nashi, guava, watermelon, honey dew melon, kiwifruit and starfruit and peaches.

Vegetables

A wide variety of minimally processed vegetables can be treated according to this invention the apple formula may be used or one of the formulae shown in table 4.

The solution is boiled for 3 minutes and then the other ingredients are added. Immersion of the peeled and/or cut vegetables is for 3 to 8 minutes as required and then drained prior to packaging.

Formula 3 was particularly suitable for potatoes, suedes, parsnip, broccolli, cauliflower, pumpkin, chocos, chopped beans and shelled peas.

The shelf life of vegetables treated with these solutions by immersion for 5 to 10 minutes followed by drying was more than 3 weeks.

Lettuce

Whole lettuce is washed in pure water and then 25 ml of the following formula was injected into the stem of the lettuce.

5 ml folic acid 5 g calcium ascorbate 60 mg of enzogenol 2.5 g of barley green or spiralina chlorophyll extract.

A shelf life in excess of 21 days was achieved with this method.

Cut Flowers

TABLE 4

| formula | Solution | Ascorbic acid source | Flavonoid | other |
|---|---|---|---|---|
| 1 | 200 ml water+ | 5 g ascorbic acid | 50 mg grapeseed oil or enzogenol | 5 ml grapeseed oil |
| 2 [celery] | 200 ml water 5 mg green tea extract | 5–10 g calcium ascorbate | 60 mg enzogenol | |
| 3 | 200 ml water | 50 mg alpha lipoic acid | 25 mg hesperidin | 5 mg citric or tartaric acid + 2 mg folic cid |
| 4 | 6 juniper berries in 150 ml water | 5 g calcium ascorbate | 500 1 U d-alpha tocopherol | 5 mg zinc gluconate |

Formula 1 is used with carrots that have been sliced or diced

The vegetable formula or 5 g of potassium ascorbate and 20 mg of enzogenol in 2 liters of water has been found to maintain the freshness of cut flowers when used as the solution in vases.

From the above it can be seen that this invention provides a unique way of using naturally occurring compounds to extend the shelf life of minimally processed vegetables. Variations and additions to the formula and process can be made without departing from the inventive concept as disclosed herein.

What is claimed is:

1. A process of extending the useful shelf life of peeled and cut fruits and vegetables comprising the steps of:

forming an aqueous solution which contains a flavonoid derived from the seeds, fruit or bark of plants in association with a food grade antioxidant, the ratio by weight of flavonoid to antioxidant being 1:50 to 1:150;

dipping, spraying or coating cut or peeled fruits and vegetables with the solution; and retaining the moisture content of the peeled and cut fruits and vegetables during a packaging operation.

2. A process as claimed in claim 1, wherein the flavonoid content in the solution is from 0.01 to 0.1% by weight.

3. A process as claimed in claim 1, wherein the flavonoid is selected from the group comprising: acerola, quercitin, hesperidin, rutin and flavonoid rich extracts from pine bark, grape seeds, citrus seeds, cranberries, Juniper berries and rosehips.

4. A process as claimed in claim 1, wherein the solution additionally contains alpha lipoic acid.

5. A process as claimed in claim 1, wherein the food grade antioxidant is selected from the group comprising ascorbic acid, erythorbic acid, lipoic acid and salts thereof.

6. A process of extending the useful shelf life of oranges juice comprising the steps:

extracting the juice from oranges; and adding alpha lipoic acid and a flavonoid derived from the seeds, fruit or bark of plants to the juice.

7. A process as claimed in claim 6, where the oranges are navel orange.

8. Orange juice produced by the process comprising the steps:

extracting the juice from oranges; and adding alpha lipoic acid and a flavonoid derived from the seeds, fruit or bark of plants to the juice.

9. Peeled and cut fruits and vegetables prepared by the process comprising the steps:

peeling and cutting fruits and vegetables; and dipping, spraying or coating the fruits and vegetables with an aqueous solution which contains a flavonoid derived from the seeds, fruit or bark of plants in association with a food grade antioxidant, the ratio by weight of flavonoid to antioxidant being 1:50 to 1:150.

10. A fruit and vegetable preservative composition comprising a flavonoid derived from the seeds, fruit or bark of plants in association with a food grade antioxidant selected from the group comprising ascorbic acid, erythorbic acid, lipoic acid and salts thereof, the ratio by weight of flavonoid to antioxidant being 1:50 to 1:150.

* * * * *